US008293534B2

(12) United States Patent  
Hallinan

(10) Patent No.: US 8,293,534 B2  
(45) Date of Patent: *Oct. 23, 2012

(54) METHOD FOR QUANTIFYING PERMANGANATE-REDUCING COMPOUNDS

(75) Inventor: Noel Hallinan, Loveland, OH (US)

(73) Assignee: Lyondell Chemical Technology, L.P., Houston, TX (US)

( * ) Notice: Subject to any disclaimer, the term of this patent is extended or adjusted under 35 U.S.C. 154(b) by 315 days.

This patent is subject to a terminal disclaimer.

(21) Appl. No.: 12/589,930

(22) Filed: Oct. 30, 2009

(65) Prior Publication Data

US 2011/0101233 A1    May 5, 2011

(51) Int. Cl.
G01N 33/00  (2006.01)
G01N 21/00  (2006.01)
(52) U.S. Cl. .............................. 436/2; 436/84
(58) Field of Classification Search ............... 436/2, 84, 436/172; 562/608
See application file for complete search history.

(56) References Cited

U.S. PATENT DOCUMENTS

| 7,208,625 | B1 | 4/2007 | Wang et al. |
| 2011/0104807 | A1* | 5/2011 | Hallinan ........................ 436/2 |

OTHER PUBLICATIONS

"A New System for automatic measurement of Permanganate Time," *Laboratory Automation and Information Management*, 34, 1999, pp. 57-67.

Kenneth A. Rubinson, "Chapter 7. Introduction to Spectrometry," *Chemical Analysis*, 1986, pp. 615-661.

R. A. Friedel and J. A. Queiser, "Inorganic and Organic Analysis by Infrared Spectrometry in Coal Problems," *ACS Preprints—Fuel Chemistry Division Symposium*, 10(3), 1966, pp. 1-6, available at http://www.anl.gov/PCS/acsfuel/preprint%20archive/Files/10_3_NEW%20YORK_0966_012.

* cited by examiner

*Primary Examiner* — Lyle Alexander
*Assistant Examiner* — Dwan A Gerido

(57) ABSTRACT

A method for quantifying the permanganate-reducing compounds (PRCs) in an acetic acid sample is disclosed. The method comprises establishing a correlation between permanganate absorbances of standard samples and their PRC contents and determining the PRC content of the acetic acid sample by measuring its permanganate absorbance of a reaction mixture containing a standard permanganate solution and the acetic acid sample. The permanganate absorbance is obtained by subtracting the manganese dioxide absorbance from the absorbance of the mixture.

8 Claims, 6 Drawing Sheets

METHOD FOR QUANTIFYING PERMANGANATE-REDUCING COMPOUNDS

FIELD OF THE INVENTION

The invention relates to quantifying the permanganate-reducing compound content of an acetic acid sample.

BACKGROUND OF THE INVENTION

Acetic acid produced by the methanol carbonylation process contains oxidizable impurities such as aldehydes (see, e.g., U.S. Pat. No. 7,208,625). A qualitative test, called the Permanganate Time (PT), is used to determine the product quality. The PT test has a Pass or Fail designation. To perform the PT test, a known amount of $KMnO_4$ is added to a known amount of acetic acid. To pass the test, the initial pink color of $KMnO_4$ must not have completely dissipated after two hours. $KMnO_4$, a strong oxidizing agent, can oxidize aldehydes and other oxidizable compounds (also called "permanganate-reducing compound" or PRC). In doing so, $MnO_4^-$ is reduced to colorless $Mn^{2+}$ according to the following reaction:

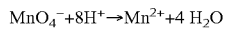

$$MnO_4^- + 8H^+ \rightarrow Mn^{2+} + 4 H_2O$$

As PT is a visual test, there is considerable operator subjectivity involved in determining the point at which the pink color has disappeared. This visual test is further complicated and compromised by the fact that $Mn^{2+}$ is relatively unstable and is prone to oxidation by $MnO_4^-$ to form manganese dioxide ($MnO_2$), a brownish/yellowish species, through the following reaction:

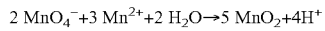

$$2 MnO_4^- + 3 Mn^{2+} + 2 H_2O \rightarrow 5 MnO_2 + 4H^+$$

$MnO_2$ in the reaction mixture interferes with the observation of the pink color. To overcome this difficulty, a recent report discloses a spectrophotometric method for correlating an objective colorimetric measurement with a subjective visual measurement and determining PT based on instrumental analysis ("A New System For Automatic Measurement of Permanganate Time," *Laboratory Automation and Information Management*, 34, 1999, 57-67). However, the report does not teach quantitatively determining the PRC content (or concentration) of an acetic acid sample.

SUMMARY OF THE INVENTION

The invention is a method for quantifying the permanganate-reducing compounds (PRCs) in an acetic acid sample. The method comprises establishing a correlation between the permanganate absorbances of standard samples and their PRC contents by (i) preparing two or more standard samples with known PRC contents; (ii) adding a known amount of a standard permanganate solution to each standard sample to form a mixture; (iii) for each standard sample, measuring the absorbance of the mixture at a selected wavelength in the range of 460 to 580 nm at a set reaction time; (iv) for each standard sample, determining the permanganate absorbance by the difference between the absorbance of the mixture and the manganese dioxide absorbance; and (v) establishing a correlation between the permanganate absorbances of the standard samples and their PRC contents. The PRC content of the acetic acid sample is determined from the correlation and its permanganate absorbance that can be determined by repeating steps (ii) to (iv) above.

DETAILED DESCRIPTION OF THE INVENTION

The invention is a method for quantifying the permanganate-reducing compounds (PRCs) in an acetic acid sample. Acetic acid produced by the methanol carbonylation process often contains aldehydes, including acetaldehyde, propionaldehyde, butyraldehydes, crotonaldehyde, their derivatives such as 2-ethyl crotonaldehyde, 2-ethyl butyraldehyde, and the like. In addition to aldehydes, an acetic acid sample may contain other compounds that can be oxidized by permanganate (see, e.g., U.S. Pat. No. 7,208,625).

The method uses a standard permanganate solution, preferably an aqueous solution. More preferably, the standard permanganate solution is an aqueous solution of potassium, sodium, ammonium, or alkylammonium permanganate salt. An aqueous potassium permanganate solution is most preferred.

The method comprises preparing two or more standard samples with known PRC contents. A standard sample may be prepared by mixing a solvent with a known amount of PRC. Examples of suitable solvents include water, alcohols, carboxylic acids, amides, nitriles, and the like. Preferably the solvent contains negligible amount of PRC, for example, less than 0.5 ppm equivalent crotonaldehyde, more preferably, less than 0.1 ppm equivalent crotonaldehyde. One preferred solvent is water. Conveniently, an aldehyde may be spiked in the solvent to prepare the standard samples.

A known amount of the standard permanganate solution is added to each standard sample to form a reaction mixture ("mixture"). Depending on the PRC content of the standard sample, additional solvent may be used to prepare the reaction mixture. The amount of solvent used depends on the PRC content of the acetic acid sample to be analyzed.

For each standard sample, the absorbance of the mixture (also called "mixture absorbance" or $A_{mix}$) at a selected wavelength in the range of 460 to 580 nm is measured at a set reaction time. Generally, a peak absorbance at about 506, 525, or 544 nm is measured. The reaction time between the standard permanganate solution and the standard sample is conveniently 10 to 30 min. The reaction is preferably carried out at room temperature.

Figure 1:
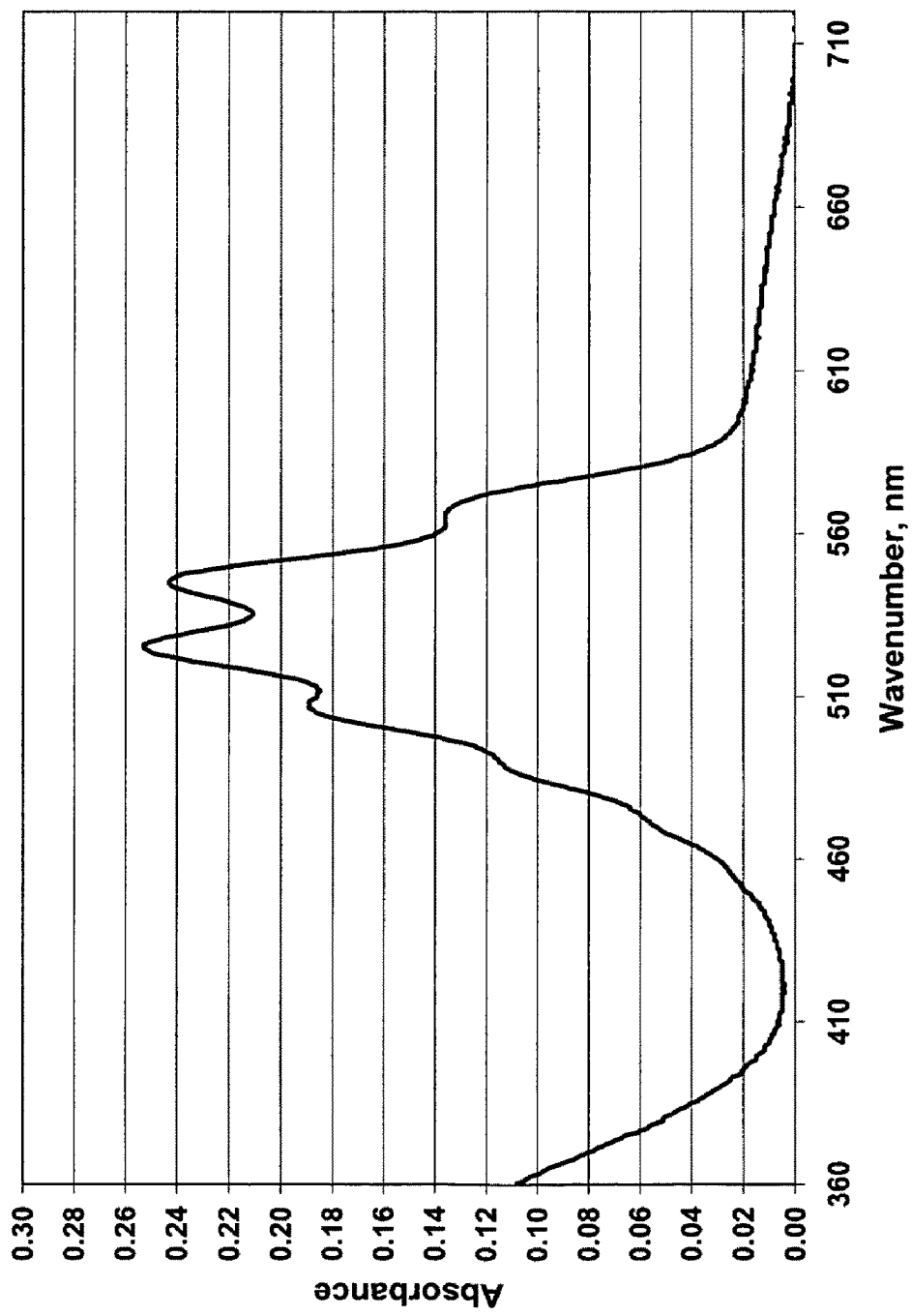
FIG. 1 is a typical UV-Vis absorption spectrum of an aqueous $KMnO_4$ solution.

Generally, an ultraviolet-visible (UV-Vis) spectrophotometer is used to measure the absorbance of the mixture. A plot of the absorbance versus wavelength is called an absorption spectrum. FIG. 1 shows a typical UV-Vis spectrum of an aqueous $KMnO_4$ solution recorded at room temperature. The solution is prepared by mixing distilled water (12 mL) and a standard $KMnO_4$ solution (0.02 N, 0.5 mL).

In a quantitative analysis, the absorbance A at a given wavelength is related to the analyte content c by Beer's law: $A=a \times b \times c$, where a is absorptivity of the analyte and b is the sample pathlength. The absorbance of a species depends on not only its concentration, but also the pathlength of the cuvette used.

Figure 2:
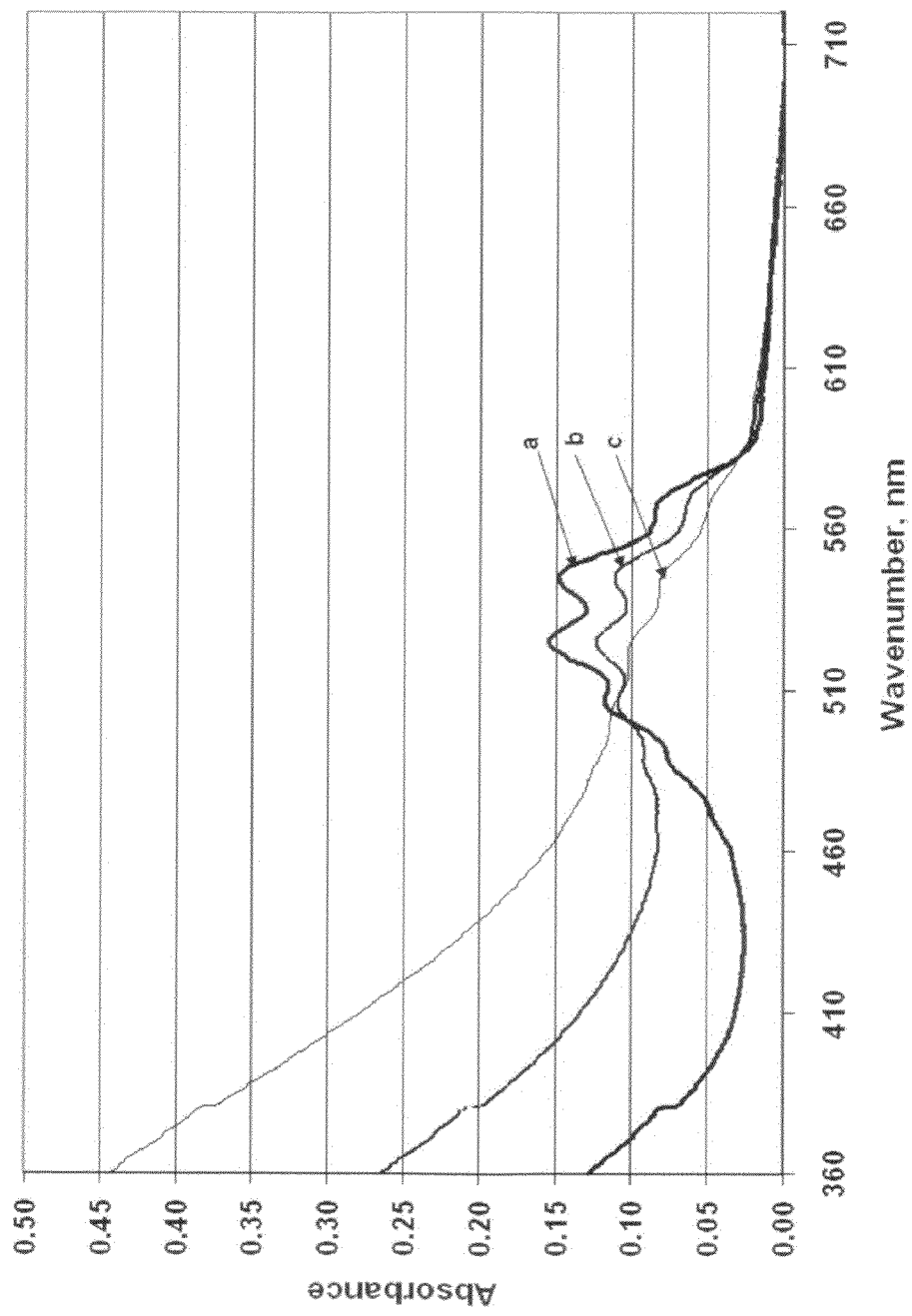
FIG. 2 shows UV-Vis absorption spectra of a mixture of an acetic acid sample (containing 15.2 ppm equivalent crotonaldehyde, 2 mL), distilled water (10 mL), and a standard $KMnO_4$ solution (0.02 N, 0.5 mL) recorded after (a) 15 min; (b) 30 min; and (c) 120 min.

When a standard permanganate solution is added to a standard sample containing PRCs, the reaction between them gives colorless $Mn^{2+}$. However, $Mn^{2+}$ can react with $MnO_4^-$ to form yellowish/brownish manganese dioxide ($MnO_2$). FIGS. 2(a), 2(b), and 2(c) are spectra of a mixture of a standard sample containing 15.2 ppm equivalent crotonaldehyde (2 mL), water (10 mL), and an aqueous $KMnO_4$ solution (0.02 N, 0.5 mL) recorded after they react for 15, 30, and 120 min, respectively. The initial permanganate concentrations in the mixtures of FIG. 1 and FIG. 2 are the same, because there is not reaction in either mixture when they are just formed. FIG. 2(a) shows a large decrease in permanganate absorbance at around 525 nm as compared to FIG. 1. However, the amount of $MnO_2$ present in the solution is not significant as indicated by the small increase of absorption at around 425 nm. This indicates that the permanganate is predominantly reduced by PRCs during the first 15 min. Spectra (b) and (c), on the other hand, show the formation of significant amounts of $MnO_2$, indicating that significant amount of permanganate is reacted with $Mn^{2+}$ to form $MnO_2$. Since the absorption of light by the $MnO_2$ and permanganate in the mixture is additive, the absorbance of the mixture, $A_{mix}$, is the sum of the permanganate absorbance ($A_{perm}$) and the absorbance due to $MnO_2$ present in the mixture ($A_{MnO2}$), i.e., $A_{mix}=A_{perm}+A_{MnO2}$.

$A_{MnO2}$ can be determined by many techniques. See K. A. Rubinson, "Chapter 7. Introduction to Spectroscopy," *Chemical Analysis* (1986) pp. 615-661). In one technique, $A_{MnO2}$ is determined by drawing a baseline across the base of a permanganate absorption band. Such a baseline correction technique was used to analyze samples containing rock dust and coal by infrared spectrometry (R. A. Friedel, J. A., Queiser, "Inorganic and Organic Analysis by Infrared Spectrometry in Coal Problems," *ACS Preprints—Fuel Chemistry Division Symposium*, 10(3), 1966, pp. 1-6, available at http://www.anl.gov/PCS/acsfuel/preprint%20archive/Files/10_3_NEW%20YORK_0966_0120.pdf). The non-specific absorption due to the coal is corrected out by drawing a baseline across the base of the absorption band of the rock dust.

Figure 3:
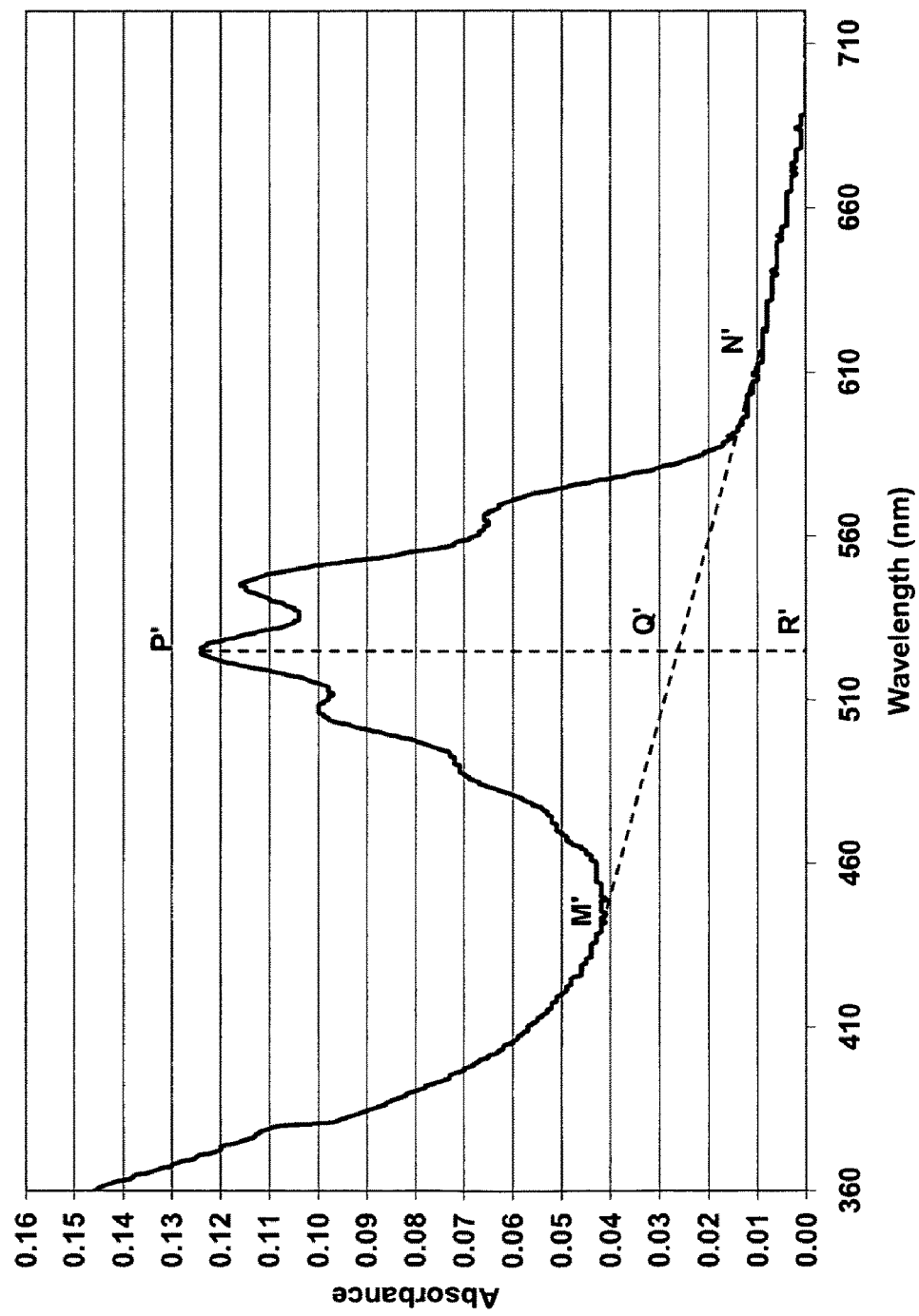
FIG. 3 is a UV-Vis spectrum of a mixture of an aqueous $KMnO_4$ solution (0.02 N, 0.5 mL), distilled water (10 mL), and an acetic acid sample (containing 20.4 ppm equivalent crotonaldehyde, 2 mL) recorded 15 min after they are mixed.

FIG. 3 is a UV-Vis spectrum of a reaction mixture recorded 15 min after the addition of a standard $KMnO_4$ solution (0.02 N, 0.5 mL) and distilled water (10 mL) in a standard sample containing 20.4 ppm equivalent crotonaldehyde (2 mL). A baseline is drawn across the base of the permanganate absorption band from 460 nm to 580 nm. The segment M'N' approximates the absorbance of $MnO_2$ between 460 nm and 580 nm. The absorbance due to $MnO_2$ in the mixture at 525 nm is represented by segment Q'R'.

Figure 4:
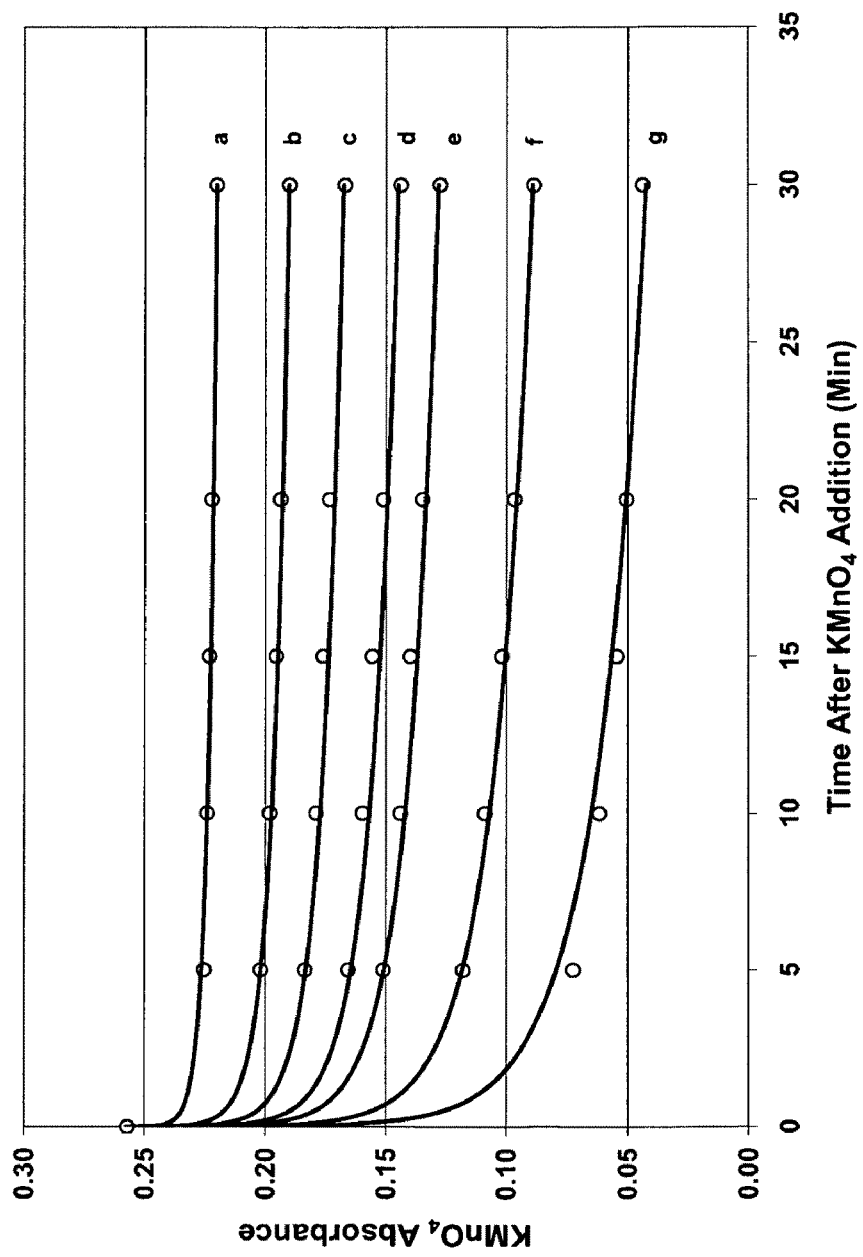
FIG. 4 shows permanganate absorbances of mixtures of standard samples as a function of the reaction time. The crotonaldehyde contents are: (a) 3.8 ppm; (b) 7.9 ppm; (c) 10.6 ppm; (d) 13.0 ppm; (e) 15.2 ppm; (f) 20.4 ppm; and (g) 25.2 ppm.

A correlation is established between the PRC contents and permanganate absorbances of the standard samples. The correlation may be a graph, a table, a mathematical equation, or the like. Preferably, a calibration curve is constructed by plotting PRC contents against their permanganate absorbances. FIG. 4 is a calibration curve constructed from the permanganate absorbances of the standard samples and their equivalent crotonaldehyde contents.

To determine the PRC content of an unknown acetic acid sample, the same amount of the standard permanganate solution, and the same amount of solvent if used, is added to the unknown acetic acid sample to form a mixture. The absorbance of the mixture ($A_{mix}$) is measured at the selected wavelength at the set reaction time. The permanganate absorbance is determined by subtracting from $A_{mix}$ the $MnO_2$ absorbance. The PRC content of the unknown sample is determined from the permanganate absorbance and the correlation obtained from the standard samples.

Since identities of aldehydes or other PRCs present in an acetic acid sample is often not known, The PRC content may be expressed in any convenient manner, e.g., in terms of —CHO content. Conveniently, the PRC content is expressed in term of an equivalent aldehyde concentration, e.g., ppm equivalent acetaldehyde, crotonaldehyde, or the like.

EXAMPLE

A Shimadzu 1700 Pharma spectrophotometer is used. All UV-Vis measurements are performed at room temperature. A standard $KMnO_4$ solution (0.02 N) is prepared by dissolving 0.63 g $KMnO_4$ (0.63 g) in distilled water (1 L).

The standard $KMnO_4$ solution (0.5 mL) is mixed with distilled water (12 mL). A portion of the mixture (3 mL) is transferred to a disposable, 1-cm pathlength polystyrene cuvette. A UV-Vis spectrum is recorded immediately, as shown in FIG. 1. Further spectra recorded over a period of one hour show no change in absorption, indicating that there is no decomposition of $KMnO_4$ in the mixture.

An acetic acid sample (Aldrich, >99.99%) is determined to have a PRC content of 3.8 ppm equivalent crotonaldehyde (see co-pending U.S. patent application Ser. No. 12/989,931, filed Oct. 30, 2009. A standard acetic acid sample (containing 20.4 ppm equivalent crotonaldehyde) is prepared by spiking crotonaldehyde in the Aldrich acetic acid. The standard sample (2 mL) is mixed with distilled water (10 mL) and the standard $KMnO_4$ solution (0.5 mL). A portion of the mixture (3 mL) is transferred to a disposable, 1-cm pathlength polystyrene cuvette. A UV-Vis spectrum is recorded after 15 min, as shown in FIG. 3. A baseline is drawn across the base of the absorption band of permanganate. The segment M'N' approximates the absorbance of $MnO_2$ between 440 nm and 600 nm. The absorbance due to $MnO_2$ in the mixture at 525 nm is represented by segment Q'R'. Thus the absorbance of the permanganate in the mixture at 525 nm after the $MnO_2$ absorption correction is represented by segment P'Q', which is 0.101.

Additional standard samples are prepared by adding known amounts of crotonaldehyde to the Aldrich acetic acid. Their equivalent crotonaldehyde contents are shown in Table 1. The permanganate absorbances of mixtures are determined by the method described as above and plotted as a function of time as shown in FIG. 4. FIG. 4 shows that most of the permanganate reaction takes place during the first 15 min.

TABLE 1

| Standard Sample | Equivalent Crotonaldehyde (ppm) |
|---|---|
| a | 3.8 |
| b | 7.9 |
| c | 10.6 |
| d | 13.0 |
| e | 15.2 |
| f | 20.4 |
| g | 25.2 |

Figure 5:
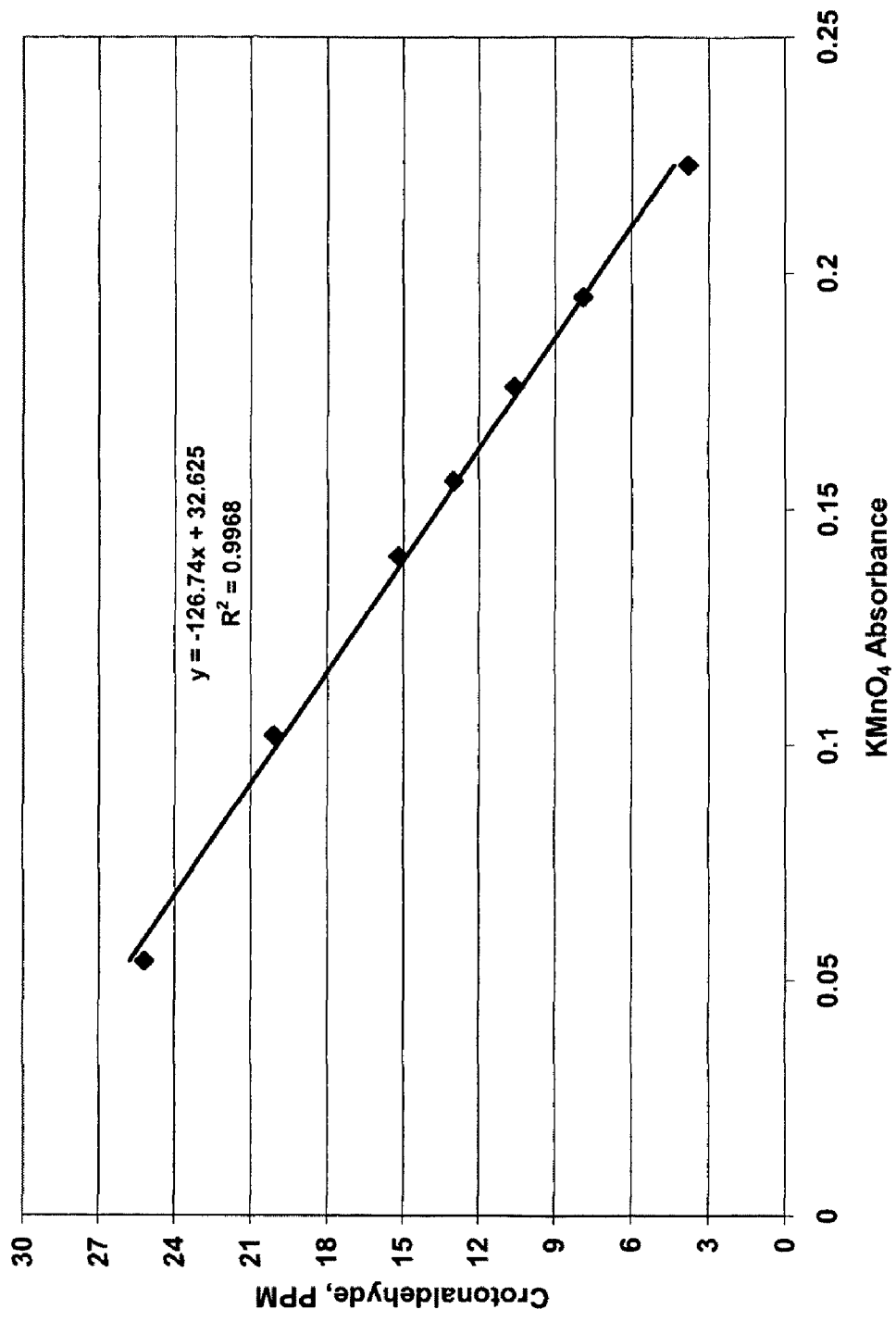
FIG. 5 is a crotonaldehyde content v. permanganate absorbance calibration curve.

Permanganate absorbances of mixtures of the standard samples at 15 min are plotted against their crotonaldehyde contents, as shown in FIG. 5. A good linear fit provides a correlation equation of the form: PRC content=−126.7× $A_{perm}$+32.6. The PRC content is expressed in equivalent crotonaldehyde (ppm).

The PRC content of an unknown acetic acid sample can be determined from the calibration curve in FIG. 5 by measuring its permanganate absorbance. One can also calculate the PRC content using the above equation.

Figure 6:
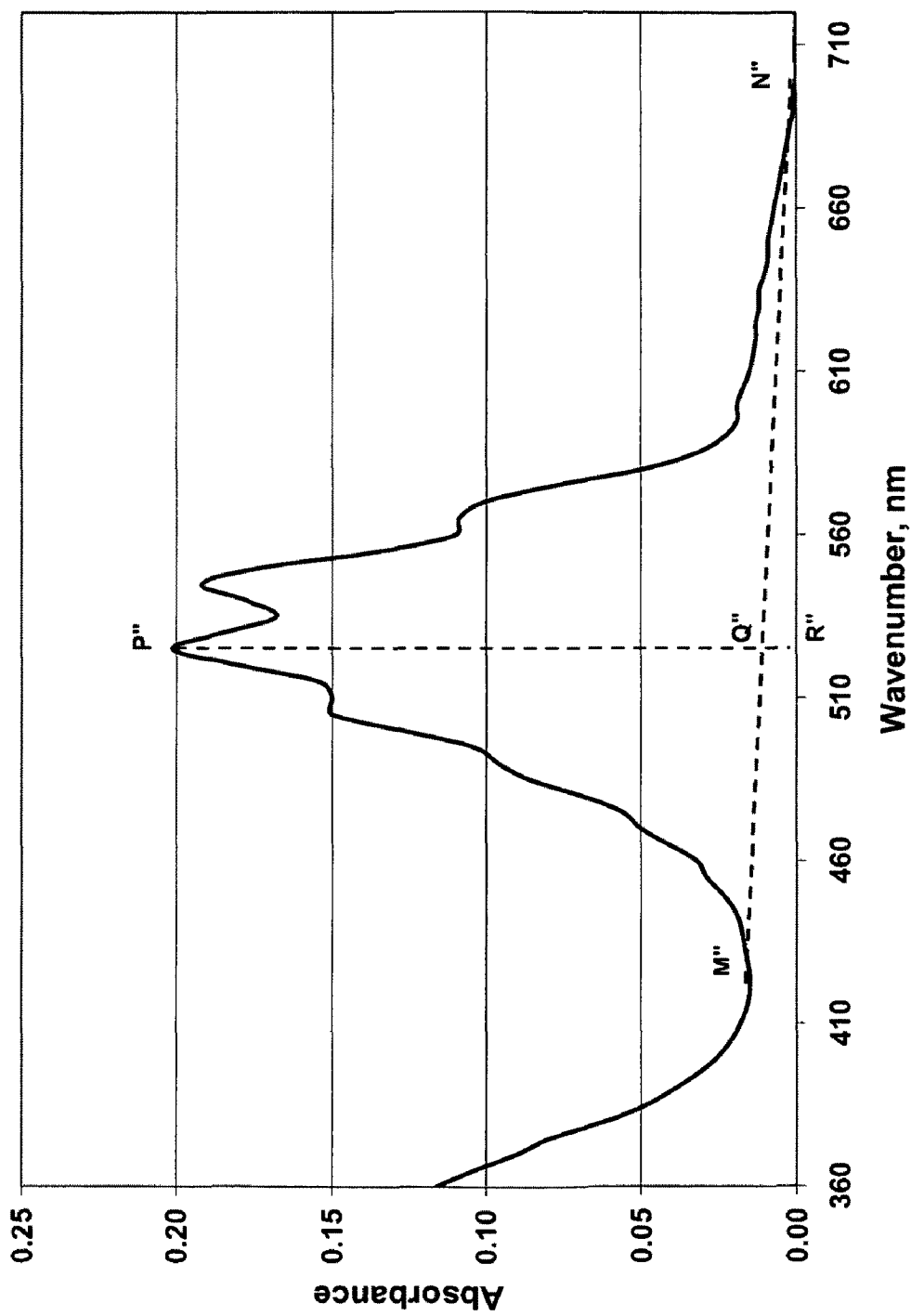
FIG. 6 is a UV-Vis spectrum of a mixture of an aqueous $KMnO_4$ solution (0.02 N, 0.5 mL), distilled water (10 mL), and an unknown acetic acid sample (2 mL) recorded 15 min after they are mixed.

An acetic acid sample of unknown PRC content (2 mL) is mixed with distilled water (10 mL) and the standard $KMnO_4$ solution (0.5 mL). A portion of the mixture (3 mL) is transferred to a 1-cm pathlength polystyrene cuvette. A UV-Vis spectrum is recorded 15 min after the mixture is made, as shown in FIG. 6. The unknown acetic acid sample has an $A_{perm}$ value of 0.188. Its PRC content is calculated to be 8.8 ppm equivalent crotonaldehyde.

I claim:

1. A method for quantifying permanganate-reducing compound (PRC) content of an acetic acid sample, comprising:
   (a) establishing a correlation between permanganate absorbances of standard samples and their PRC content by:
      (i) preparing two or more standard samples with known PRC contents;
      (ii) adding a known amount of a standard permanganate solution to each standard sample from (a)(i) to form a mixture;
      (iii) for each standard sample, measuring the absorbance of the mixture ($A_{mix}$) at a selected wavelength in the range of 460 to 580 nm at a set reaction time;
      (iv) for each standard sample, determining the permanganate absorbance ($A_{perm}$) at the set reaction time by subtracting from $A_{mix}$ the absorbance due to manganese dioxide ($A_{MnO2}$) at the selected wavelength;
      (v) establishing a correlation between permanganate absorbances and their PRC contents; and
   (b) repeating steps (a)(ii) through (a)(iv) with the unknown acetic acid sample that contains an unknown amount of PRC to determine its PRC content.

2. The method of claim 1 wherein $A_{MnO2}$ is determined by drawing a baseline across the base of a permanganate absorption band.

3. The method of claim 1 wherein the correlation is a calibration curve.

4. The method of claim 1 wherein the standard permanganate solution is a potassium permanganate solution.

5. The method of claim 1 wherein the set reaction time is from 10 to 30 min.

6. The method of claim 1 wherein a solvent is used to form the mixture.

7. The method of claim 6 wherein the solvent is selected from the group consisting of water, alcohols, carboxylic acids, amides, nitriles, and mixtures thereof.

8. The method of claim 7 wherein the solvent is water.

* * * * *